(12) United States Patent
Kooijker et al.

(10) Patent No.: US 9,486,564 B2
(45) Date of Patent: Nov. 8, 2016

(54) BREAST SHIELD FOR A BREAST PUMP

(71) Applicant: KONINKLIJKE PHILIPS N.V., Eindhoven (NL)

(72) Inventors: Klaas Kooijker, Drachten (NL); Gertrude Riette Van Der Kamp, Groningen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/361,918

(22) PCT Filed: Dec. 6, 2012

(86) PCT No.: PCT/IB2012/057010
§ 371 (c)(1),
(2) Date: May 30, 2014

(87) PCT Pub. No.: WO2013/088310
PCT Pub. Date: Jun. 20, 2012

(65) Prior Publication Data
US 2014/0323962 A1 Oct. 30, 2014

Related U.S. Application Data

(60) Provisional application No. 61/569,407, filed on Dec. 12, 2011.

(30) Foreign Application Priority Data

Dec. 12, 2011 (EP) .................................... 11192917

(51) Int. Cl.
A61M 1/06 (2006.01)

(52) U.S. Cl.
CPC ............... A61M 1/062 (2014.02); A61M 1/06 (2013.01); A61M 1/066 (2014.02)

(58) Field of Classification Search
CPC .............................. A61M 1/06; A61M 1/064
See application file for complete search history.

(56) References Cited

U.S. PATENT DOCUMENTS

| 5,941,847 A * | 8/1999 | Huber et al. ................... 604/74 |
| 6,004,288 A | 12/1999 | Hochstedler |
| 6,461,324 B1 * | 10/2002 | Schlensog ....................... 604/74 |
| 2002/0198489 A1 * | 12/2002 | Silver et al. .................... 604/74 |
| 2003/0004459 A1 * | 1/2003 | McKendry et al. ........... 604/74 |
| 2003/0073951 A1 * | 4/2003 | Morton et al. ................. 604/73 |
| 2008/0312586 A1 | 12/2008 | Thommen |
| 2011/0071466 A1 * | 3/2011 | Silver et al. .................... 604/74 |

FOREIGN PATENT DOCUMENTS

| EP | 0466462 A1 | 1/1992 |
| EP | 2172236 A1 | 4/2010 |
| WO | 9822160 A1 | 5/1998 |
| WO | 02102439 A1 | 12/2002 |
| WO | 03000313 A1 | 1/2003 |
| WO | 2004058330 A1 | 7/2004 |

* cited by examiner

Primary Examiner — Scott Medway

(57) ABSTRACT

A shield for a breast pump is disclosed. It comprises a resilient, flexible insert configured to receive a user's breast, and an adjuster operable by a user to alter the shape of the insert.

11 Claims, 3 Drawing Sheets

BREAST SHIELD FOR A BREAST PUMP

CROSS-REFERENCE TO PRIOR APPLICATIONS

This application is the U.S. National Phase application under 35 U.S.C. §371 of International Application No. PCT/IB2012/057010, filed on Dec. 6, 2012, which claims the benefit of U.S. Provisional Patent Application No. 61/569,407, filed on Dec. 12, 2011 and European Patent Application No. 11192917.0, filed on Dec. 12, 2011. These applications are hereby incorporated by reference herein.

FIELD OF THE INVENTION

The present invention relates to a shield for a breast pump having a breast receiving member to receive the breast of a user. The invention also relates to a breast pump comprising the shield of the invention.

BACKGROUND OF THE INVENTION

Breast pumps are well known devices for extracting milk from a breast of a user. A breast pump may be used if the baby or infant is not itself able to extract milk from the breast, or if the mother is separated from the baby or infant and is to be fed with breast milk by someone else. Breast pumps typically comprise a rigid, funnel-shaped shield connected to a vacuum pump having a container for collecting the milk.

The shield of a breast pump is the interface between the user's breast and nipple with the pump and so its sizing is critical to maintaining the user's comfort whilst using the device. It is also important to ensure that the vacuum seal between the breast and the shield is maintained for optimal pumping. A problem with a conventional breast pump is that it has a shield of fixed size, so it can only cater for a limited range of breast and nipple sizes. However, if the shield is too small relative to the nipple, the nipple tends to fill the available space inside the shield and is likely to touch on the sides of the shield, resulting in chafing, friction and discomfort as negative pressure generated during use of the pump draws the nipple into the shield. On the contrary, if the shield is too large relative to the nipple, then there will be more dead space inside the shield which will reduce the efficiency of the pump system and limit the negative pressure achievable. It also introduces the possibility that the nipple will be pulled deeper into the pump and that the skin on areola or breast area surrounding the nipple will be subjected to chafing.

If the breast shield is not of the optimum size in relation to the size of the breast, there is a tendency for the user to apply greater pressure to the breast pump to urge the breast shield into closer contact with their breast. However, undue pressure on the breast can have a negative effect on the milk production and comfort for the mother. Excessive pressure may also cause the breast shield to block a milk duct resulting in further discomfort and inflammation of the breast tissue. Furthermore, as breast feeding is a delicate matter and is largely influenced by hormones, undue pressure on the breasts can have a negative impact on milk generation and lactation.

An ill-fitting breast shield can cause further problems for the user. Hormones, created by the body, trigger breast milk production and the creation of these hormones depends greatly on the comfort and confidence of the user. If the user perceives the breast shield to be uncomfortable, either visually or by feel, they may loose confidence and milk production may be impaired.

Research has shown that nipple diameter and length varies throughout the population and across different geographic regions and also that the size of the nipple can be different before, during and after expressing. Therefore, as fit is an important consideration when attempting to achieve maximum comfort for a user, a breast pump shield for a breast pump that is capable of accommodating a wide range of breast and nipple sizes is desirable. Furthermore, a breast will change shape and size during lactation. It would therefore be desirable to have the ability to adjust the breast shield during use, and without having to remove the shield from the breast, to ensure that the comfort and effectiveness does not deteriorate.

It is known to provide a breast pump body with a removable shield that may be replaced with another shield of a different size. However, removable shields are generally made from a hard plastic material and do not generally offer the user an enhanced level of comfort whilst using such a device. It is also necessary to store, and have readily accessible, the alternate breast shield, which is not always desirable or convenient. Changing a breast shield is also time consuming and means that the user has to remove their breast from the shield currently in use. As the shields are of finite sizes, they do not allow precise adjustment and it is necessary for a user to be satisfied with a breast shield which is closest in size or shape to that which is actually desired.

It is also known to provide a soft elastomer liner that may be disposed within a rigid shield of a breast pump and which is designed to adapt to the contour of the breast so as to provide comfort and a vacuum seal necessary for operating the pump. The resilience and compliance of such a liner helps to provide a vacuum and milk seal around the user's breast and also reduces friction on the breast and/or nipple when the negative pressure draws the breast and nipple in a direction into the pump. A cushion or insert may be formed from silicon or thermoplastic elastomer (TPE) which, in addition to providing an enhanced level of comfort, can also provide a warmer feeling to the breast.

Although a liner may improve the comfort for a user, a breast pump shield equipped with a liner still suffers from the problem that the liner will only accommodate a relatively small range of breast and/or nipple sizes resulting in a poor fit between the breast and/or the nipple with the insert for a relatively large number of breastfeeding women, causing discomfort and poor vacuum pressure generation.

The present invention seeks to overcome or substantially alleviate the aforementioned problems.

SUMMARY OF THE INVENTION

It is known, for example from EP 2,172,236 A1, to provide a shield for a breast pump comprising a body attachable to a breast pump, a resilient, flexible insert received in the body and configured to receive a user's breast, the insert being mountable to a body and an adjuster operable by a user to alter the shape of the insert, wherein the body has a narrow, inner end for attachment to a breast pump body and a wider, outer end through which a breast is inserted into the shield, a first end of the flexible insert being immovably mounted to the wider, outer end of the body with a second end of the insert extending through the body towards its inner end.

According to the present invention, there is provided a breast shield for a breast pump characterised in that the adjuster is configured to move the second end of the insert towards said wider, outer end of the body to axially compress, and thereby change the shape of, the insert. As the shape of the insert is adjustable, the user may adapt the insert to suit the shape of their breast and so have a more comfortable pumping experience.

Adjustment of the breast shield prevents the need for interchanging breast shields for different shapes and sizes of breast. This reduces the number of components that need to be sold with a breast pump making it easier to use and cheaper to produce.

The adjuster may comprise a collar received on the inner end of the body, said second end of the insert being in contact with said collar which is configured such that rotation relative to the body in one direction moves it axially towards said wider, outer end of the body to axially compress, and thereby change the shape of, the insert. This configuration provides an easy way for a user to simply and quickly adjust the shape of the insert to suit their requirements and provides a wide range of adjustment. Preferably, the collar is configured such that rotation relative to the body in the opposite direction moves it axially away from said wider, outer end of the body, the resilience of the insert causing it to expand in an axial direction and thereby change the shape of the insert. This enables the user to simply adjust the shape of the insert back to its original form, i.e. the user is quickly able to appreciate that the shape can be adjusted simply by turning the collar in opposite directions.

The collar may be threadingly received on the inner end of the body. This enables rotation of the collar by the user to be translated into axial movement of the second end of the insert towards, and away from, the first end of the insert.

Preferably, a thread is formed on an inner surface of the collar and at least one radially extending thread follower on the outside of the body, the follower cooperates with the thread to enable the collar to rotate relative to the body. The thread follower may simply be a post extending outwardly from the body which locates in a helically shaped groove in the collar.

In a preferred embodiment, the collar extends beyond the inner end of the body and comprises a radially inwardly extending shoulder, said second end of the insert being in contact with said shoulder. The second end of the insert is in contact with the collar, but is not attached to the body. This means that the second end of the insert will move axially within the body in response to rotation of the collar in either direction, thereby moving it towards, or away from, the fixed first end of the insert. This movement has the result of deforming or changing the shape of the insert.

Preferably, the body has a generally conical portion that narrows from its wider outer end in a direction towards its inner end and a substantially cylindrical portion that extends from said conical portion to said inner end, said insert also narrowing in the same direction and having a substantially cylindrical tubular section extending through the substantially cylindrical portion of the retaining element. The generally conical portion of the body supports the conical portion of the insert. Similarly, the cylindrical portion receives the collar and guides movement of the second end of the insert within the body.

The substantially cylindrical portion of the body may have openings therein. In which case, the tubular section of the insert may also have radially outwardly extending protrusions. The protrusions locate in said openings when the insert is received in the body. This prevents rotation of the insert relative to the body when adjustment is being carried out as a result of rotation of the collar.

Preferably, the generally conical portion of the body comprises a circular frame to which the first end of the insert is attached and a plurality of arms extending radially inwardly towards each other at an angle away from said frame, the substantially cylindrical portion comprising generally axially extending tips to the end of each arm, said openings being formed by spaces between said tips. As the body is formed from a frame, the amount of material used in its construction is reduced. It is also lighter and easier to clean.

The section of the insert that narrows from the wider, outer end of the body towards its tubular section may comprise a series of ribs in the wall of the insert, each rib being parallel to each other and to a plane extending across the wider outer end of the retaining element. This increases the flexibility of the insert, which can fold more easily between the ribs when its shape is being adjusted.

A flexible liner may be removably receivable in the insert. As the liner will form the material that makes direct contact with the breast tissue, it may further provide the user with an enhanced level of comfort and as it can be removed easily will also make the breast pump easier to clean.

According to the invention, there is also provided a pump body having a milk receiving inlet, including a shield according to the invention for attachment to said milk receiving inlet.

BRIEF DESCRIPTION OF THE DRAWINGS

Preferred embodiments of the invention will now be described, by way of example only, with reference to the accompanying drawings, in which.

DETAILED DESCRIPTION

Figure 1:
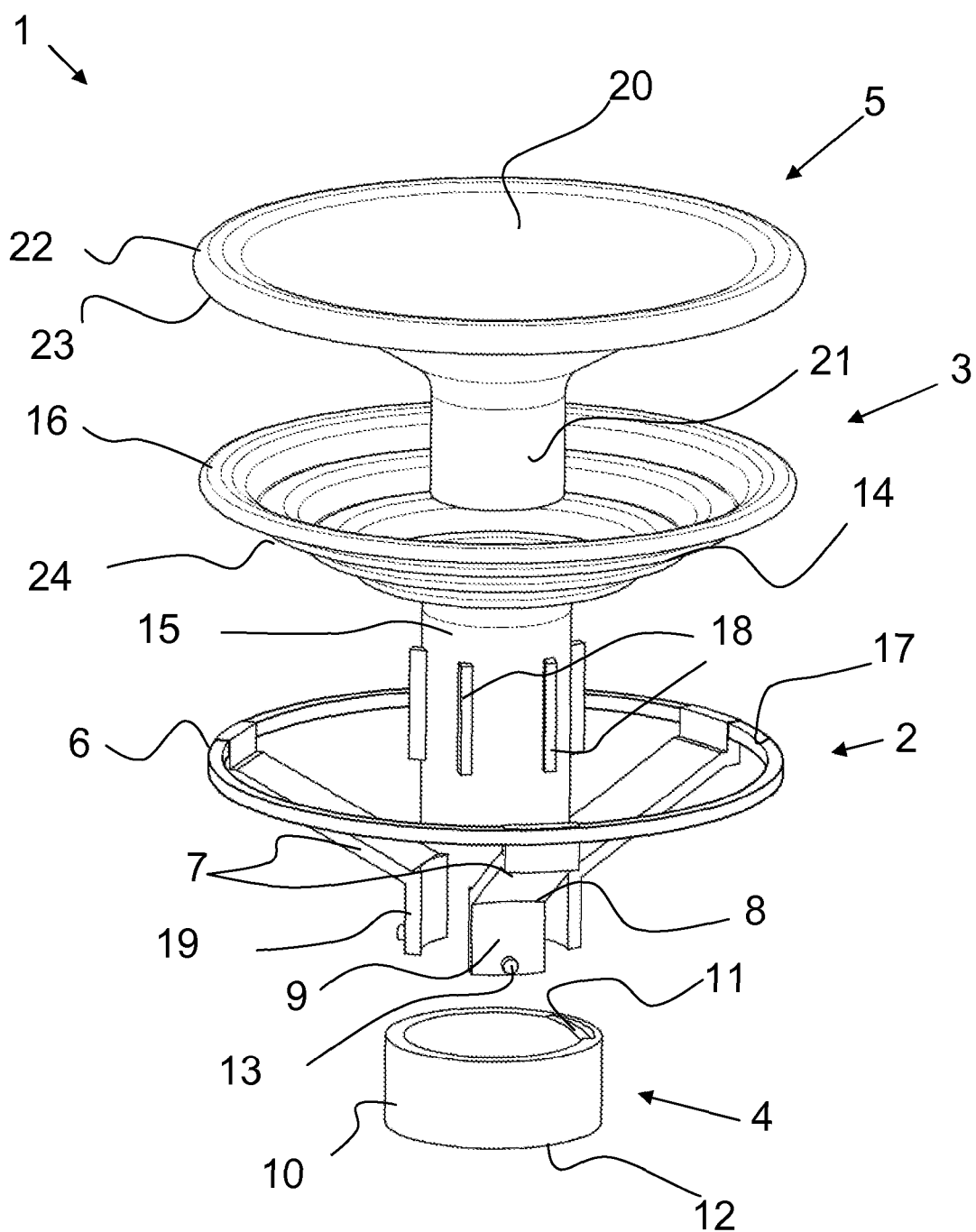
FIG. 1 shows an exploded view of a first embodiment of the breast shield according to the invention.

Referring to the drawings, FIG. 1 shows a first embodiment of the adjustable breast shield 1, comprising a rigid body 2, a flexible insert 3, an adjuster including an adjusting collar 4 and a removable liner 5.

The rigid body 2 comprises a wider, outer end defined by a frame having a ring 6 and three arms 7 extending downwardly from the upper ring 6 at an angle towards the axis of the upper ring 6 to form a generally conical or funnel-like shape. The distal ends 8 of the arms 7 each have tips 9 that extend substantially axially to form a tubular-shaped portion with a smaller internal diameter than the upper ring 6. The tips 9 terminate at a second, inner end of the body 2 which can be rigidly, and releasably, connected to a milk inlet of a breast pump body (not shown).

The adjustment collar 4 comprises an annular body 10 with an internal thread 11 and a radially inwardly extending internal lip or shoulder 12 at its lower end. The opposite end of the collar couples to the body 2 over the tips 9 and extends beyond the second, inner, end of the body 2 with the lip 12 extending radially inwardly across the second end of the body 2 and beyond an inner surface of each of the tips 9.

The tips 9 of the body 2 comprise thread engagement protrusions or members 13 extending radially outwardly from their outer surface that engage with an internal thread 11 formed on an inner surface of the adjusting collar 4 so that, when the adjusting collar 4 is turned, the thread 11 and the thread engagement members 13 cooperate so that the collar 4 moves in an axial direction along the tips 9 of the body 2, the direction of axial movement depending on the direction of rotation of the collar 4 relative to the body 2.

Rotation of the collar 4 is limited, in one direction, as a result of the tips 9 coming into contact with the lip 12 on the adjusting collar 4 and, in the other direction, by an end of the threaded part 11 formed on the adjusting collar 4.

The flexible insert 3 comprises a deformable cone 14 having a first end immovably and releasably coupled to the wider, outer end of the body 2. The insert 3 extends through the body 2 towards its second end and narrows into a tubular section 15. The deformable cone 14 may comprise a plurality of folds 24 that open and close to provide increased flexibility in the cone 14. These folds may be formed between a series of circular ribs parallel to each other and to a plane extending across the wider, outer end of the body 2.

When assembled, the first end of the insert 3 is attached to the outer end of the body 2 and the second end extends into the body 2 with the tubular section 15 of the flexible insert 3 being slideably received through, and guided by, the tubular portion 9 of the rigid body 2, formed by the tips 9. The second end of the insert 3 contacts the internal lip 12 of the adjusting collar 4 that protrudes radially inwardly beyond the inner surface of the tips 9.

The tubular section 15 comprises a plurality of radially extending ribs 18 on its external face that each extend longitudinal to the axis of the tubular section 15 and are positioned so that they locate in the gaps between the tips 9. The ribs 18 engage side edges 19 of the tips 9 and prevent rotation of the flexible insert 3 with respect to the rigid body 2.

The arrangement is such that, as the adjustment collar 4 is turned in a first direction, the collar 4 moves axially towards the outer end of the body 2. As the second end of the insert 3 is in contact with the collar 4, via the lip 12, the insert 3 is resiliently deformed under axial compression, i.e. the distance between its fixed first end, and its movable second end is reduced. This changes the shape of the deformable cone 14 of the insert 3 from a position, as shown in FIG. 2a, in which it generally lies against and conforms to the shape of the body 2, into the shape shown in FIG. 2b, in which the conically shaped portion 14 has been substantially flattened.

Similarly, when the adjustment collar 4 is turned in the opposite direction, it moves axially towards the inner end of the body 2. This increases the distance between the first and second ends of the insert 3, releasing the insert 3 and allowing it to regain its original shape, as shown in FIG. 2a.

Figure 2A:
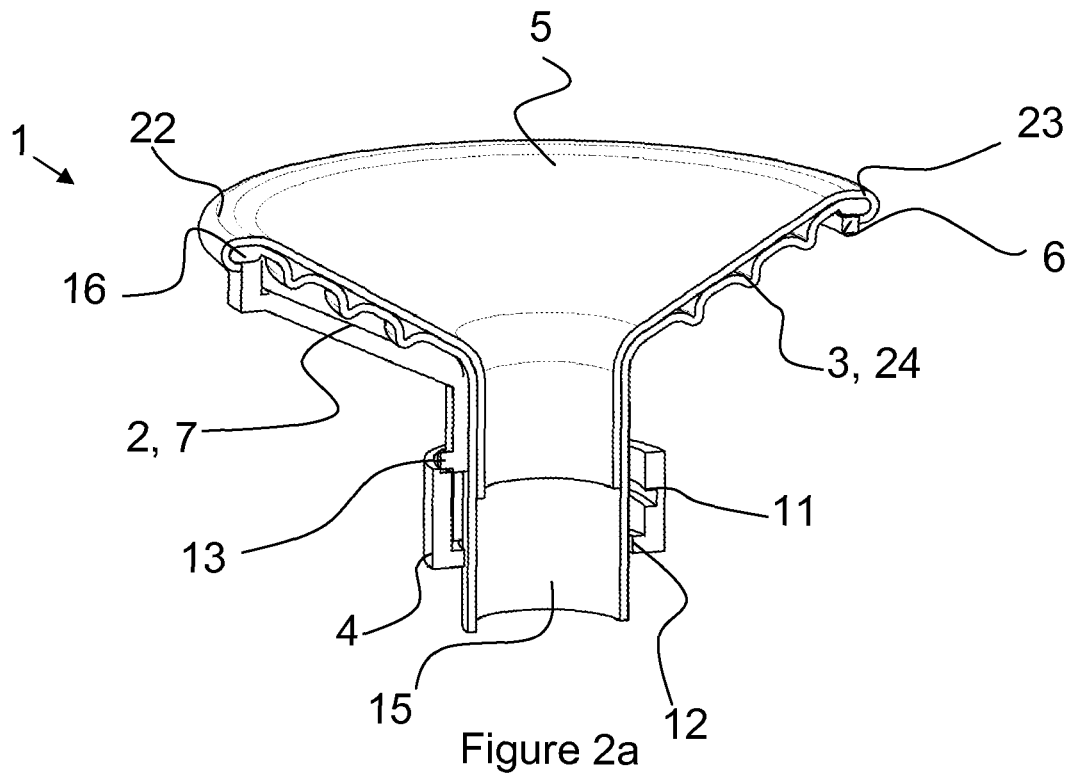
FIG. 2a shows a side view of the embodiment described in FIG. 1, the breast shield is adjusted to a first maximum position.
Figure 2B:
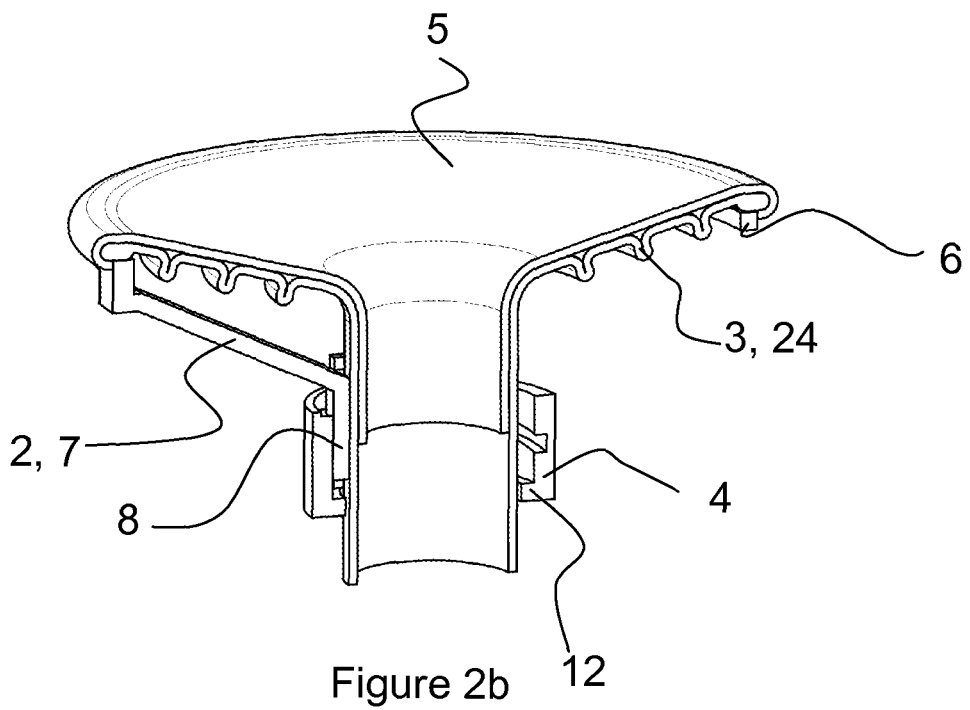
FIG. 2b shows a side view of the embodiment described in FIG. 1 and FIG. 2a, the breast shield is adjusted to a second maximum position.

The collar 4 may be a friction fit on the tips 9 of the body 2, so that the insert 3 may be positioned at any location between the two extremes shown by FIGS. 2a and 2b, thereby enabling a user to select the most appropriate shape for the insert 3 to accommodate their breast size.

As the ribs 18 cooperate with the side edges of the tips 9, rotation of the flexible insert 3 is prevented.

The removable liner 5 is made of a flexible material and is inserted into the insert 3 so as to cover the inner face of the flexible insert 3. The liner 5 provides the direct interface to the breast and provides a removable part for cleaning purposes, although the entire shield may be also be disassembled for replacement of parts or for cleaning. The liner 5 comprises a conical portion 20 and a cylindrical portion 21 and closely matches the interior form of the flexible insert 3. The peripheral edge 22 of the liner 5 has a folded over lip 23 that is hooked over the edge 16 of the flexible insert 3 to fix the liner 5 and the outer edge 16 of the cone 14 of the flexible insert 3 to the upper ring 16.

Figure 3:
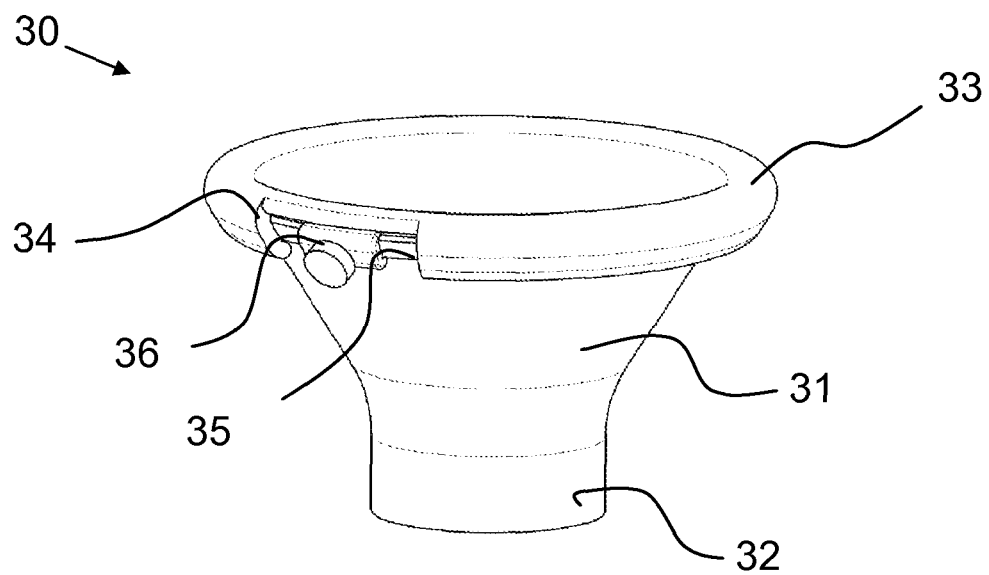
FIG. 3 shows an example of a breast shield for background information only.

FIG. 3 shows an example of an adjustable breast shield which is described for background information only. The adjustable breast shield 30 comprising a flexible conical body portion 31, a tubular portion 32 extending from the smaller end of the conical body 31 and an adjustable diameter collar 33 around the larger end of the conical body 31.

The adjustable diameter collar 33 comprises an incomplete loop with ends 34, 35 and a mechanism 36 to either pull together or push apart the ends 34, 35 of the incomplete loop, so changing the diameter of the loop. As the diameter of the outer collar 33 is adjusted the shape of the conical body 31 will change in a radial direction. If the diameter is made larger then the cone becomes flatter, and vice versa. The limits of the screw mechanism 36 limit the amount of adjustment possible. The conical body 31 is made of an elastically deformable material and is at the smallest adjustment size when in its natural state, i.e. not under any force. The mechanism 36 can be adjusted to increase the diameter of the outer ring 33 and elastically stretch the conical body 31 until the required breast shield shape is achieved. The mechanism is finger operated and an adjustment knob can be turned by a user to change the size of the insert.

The breast shield 30 is attachable to a supporting body (not shown in FIG. 3).

Figure 4:
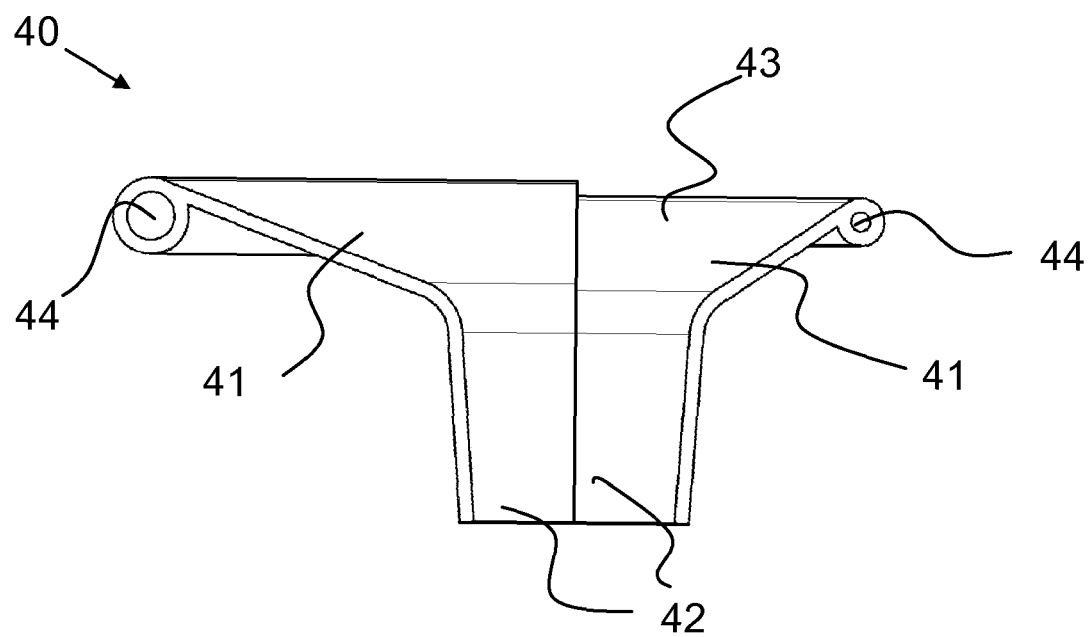
FIG. 4 shows a cross-sectional view of an example of a breast shield, for background information only showing two different states of adjustment.

FIG. 4 shows another example of an adjustable breast shield 40 which is described for background information. More specifically, it shows a sectional view of two halves at different stages of adjustment.

The adjustable breast shield of FIG. 4 comprises a flexible conical body 41, a tubular portion 42 extending from the smaller end of the conical body 41 and an adjustable diameter ring 43 on the larger, outer edge of the conical body 41. In this example the adjustable diameter ring comprises an inflatable tube 44 that is attached to, or integrally formed with, the larger edge of the conical body 41. Means for inflating the tube 44 may be a hand, or small electric, air pump or the tube 44 may be inflated by a one-way mouth air valve. It is envisaged that a release valve is included to allow the tube 44 to be deflated when required.

The conical body 41 is made of an elastically deformable material. The right hand side of FIG. 4 shows the third example of the adjustable breast shield 40 with little or no inflation of the adjustable diameter ring 43. In this state the conical body 41 is in its natural state with no elastic deformation. This is the smallest size of adjustment that can be achieved. The left hand side of the example of FIG. 4 shows the adjustable breast shield when the adjustable diameter ring 43 has been inflated, showing the increase in the size of the breast shield. The conical body 41 has been elastically enlarged.

Although FIG. 4 has been described with reference to an inflatable ring 43 that is integral with the conical body 41, it will be appreciated that the inflatable element may be entirely separate from both the body and the insert and form a separate component that is received between the body and the insert and is inflated in order to change the shape of the insert.

The breast shield 40 is attachable to a supporting body (not shown in FIG. 4).

It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

Other modifications and variations falling within the scope of the claims hereinafter will be evident to those skilled in the art.

The invention claimed is:

1. A shield for a breast pump comprising a resilient, flexible insert configured to receive a user's breast, a body attachable to a breast pump, the insert being mounted to the body and an adjuster operable by a user to alter the shape of the insert, wherein the body has a narrow, inner end for attachment to a breast pump body and a wider, outer end through which a breast is inserted into the shield, a first end of the flexible insert being immovably mounted to the wider, outer end of the body with a second end of the insert extending through the body towards its inner end, characterised in that the adjuster is configured to move the second end of the insert towards said wider, outer end of the body to axially compress, and thereby change the shape of, the insert,
   wherein the body has a generally conical portion that narrows from its wider outer end in a direction towards its inner end and a substantially cylindrical portion that extends from said conical portion to said inner end, said insert also narrowing in the same direction and having a substantially cylindrical tubular section extending through the substantially cylindrical portion of the body,
   wherein the generally conical portion of the body comprises a circular frame to which the first end of the insert is attached and a plurality of arms extending radially inwardly towards each other at an angle away from said frame.

2. A shield for a breast pump, according to claim 1, wherein the adjuster comprises a collar received on the inner end of the body, said second end of the insert being in contact with said collar which is configured such that rotation relative to the body in one direction moves it axially towards said wider, outer end of the body to axially compress, and thereby change the shape of, the insert.

3. A shield for a breast pump according to claim 2, wherein the collar is configured such that rotation relative to the body in the opposite direction moves it axially away from said wider, outer end of the body, the resilience of the insert causing it to expand in an axial direction and thereby change the shape of the insert.

4. A shield for a breast pump according to claim 2, wherein the collar is threadingly received on the inner end of the body.

5. A shield for a breast pump according to claim 4, comprising a thread on an inner surface of the collar and at least one radially extending thread follower on the outside of the body that cooperate with each other to enable the collar to rotate relative to the body.

6. A shield for a breast pump according to claim 3, wherein the collar extends beyond the inner end of the body and comprises a radially inwardly extending shoulder, said second end of the insert being in contact with said shoulder.

7. A shield for a breast pump comprising a resilient, flexible insert configured to receive a user's breast, a body attachable to a breast pump, the insert being mountable to the body and an adjuster operable by a user to alter the shape of the insert, wherein the body has a narrow, inner end for attachment to a breast pump body and a wider, outer end through which a breast is inserted into the shield, a first end of the flexible insert being immovably mounted to the wider, outer end of the body with a second end of the insert extending through the body towards its inner end, characterised in that the adjuster is configured to move the second end of the insert towards said wider, outer end of the body to axially compress, and thereby change the shape of, the insert,
   wherein the body has a generally conical portion that narrows from its wider outer end in a direction towards its inner end and a substantially cylindrical portion that extends from said conical portion to said inner end, said insert also narrowing in the same direction and having a substantially cylindrical tubular section extending through the substantially cylindrical portion of the body,
   wherein the adjuster comprises a collar received on the inner end of the body, said second end of the insert being in contact with said collar which is configured such that rotation relative to the body in one direction moves it axially towards said wider, outer end of the body to axially compress, and thereby change the shape of, the insert,
   wherein the substantially cylindrical portion of the body has openings therein, and the tubular section of the insert has radially outwardly extending protrusions,
   wherein the protrusions locate in said openings when the insert is received in the body to prevent rotation of the insert relative to the body,
   wherein the generally conical portion of the body comprises a circular frame to which the first end of the insert is attached and a plurality of arms extending radially inwardly towards each other at an angle away from said frame, the substantially cylindrical portion comprising generally axially extending tips to the end of each arm, said openings being formed by spaces between said tips.

8. A shield for a breast pump according to claim 1, wherein the substantially cylindrical portion of the body has openings therein, and the tubular section of the insert has radially outwardly extending protrusions, wherein the protrusions locate in said openings when the insert is received in the body to prevent rotation of the insert relative to the body.

9. A shield for a breast pump according to claim 1, wherein the section of the insert that narrows from the wider, outer end of the body towards its tubular section comprises a series of ribs in the wall of the insert, each rib being parallel to each other and to a plane extending across the wider outer end of the retaining element.

10. A shield for a breast pump according to claim 1, wherein the first portion of the body and the section of the insert that narrows from the wider, outer end of the body towards its tubular section are funnel shaped.

11. A breast pump comprising a pump body having a milk receiving inlet, including a shield according to claim 1 for attachment to said milk receiving inlet.

\* \* \* \* \*